United States Patent [19]

Tsuchihashi et al.

[11] 4,340,740

[45] Jul. 20, 1982

[54] ALPHA-THIO-ALPHA-ARYL-SUBSTITUTED ALKANONITRILE AND PROCESS FOR PREPARING ALPHA-ARYL-SUBSTITUTED ALKANONITRILE THEREFROM

[75] Inventors: Genichi Tsuchihashi, Tama; Shuichi Mitamura, Sagamihara; Katsuyuki Ogura, Narashino, all of Japan

[73] Assignee: Sagami Chemical Research Center, Tokyo, Japan

[21] Appl. No.: 169,193

[22] Filed: Jul. 15, 1980

[30] Foreign Application Priority Data

Jul. 16, 1979 [JP] Japan .................................. 54/89357
Jul. 19, 1979 [JP] Japan .................................. 54/90959
Mar. 28, 1980 [JP] Japan .................................. 55/38954

[51] Int. Cl.³ ........................................ C07D 277/74
[52] U.S. Cl. ............................... 548/169; 260/465 D; 260/465 F; 548/170
[58] Field of Search ........... 260/465 F, 465 D, 465 E; 548/169, 170

[56] References Cited

U.S. PATENT DOCUMENTS

| | | | |
|---|---|---|---|
| 3,413,309 | 11/1968 | Makosza et al. | 260/465 F |
| 3,600,437 | 8/1971 | Marshall . | |
| 3,649,679 | 3/1972 | Marshall . | |
| 3,855,265 | 12/1974 | Cresswell et al. | 260/465 F |
| 4,035,376 | 7/1977 | Janssen et al. | 260/465 D |
| 4,070,177 | 1/1978 | Nishiyama et al. | 260/465 F |
| 4,085,147 | 4/1978 | Rosinger et al. . | |
| 4,108,904 | 8/1978 | Brown et al. . | |
| 4,233,054 | 11/1980 | Szczepanski et al. | 260/465 D |

FOREIGN PATENT DOCUMENTS

| | | |
|---|---|---|
| 2746754 | 4/1978 | Fed. Rep. of Germany . |
| 1164585 | 9/1969 | United Kingdom . |
| 1360560 | 7/1974 | United Kingdom . |

OTHER PUBLICATIONS

Biehl et al., J. Org. Chem., 31, 602, (1966).

*Primary Examiner*—Ethel G. Love
*Attorney, Agent, or Firm*—Wenderoth, Lind & Ponack

[57] ABSTRACT

An alpha-thio-alpha-aryl-substituted alkanonitrile of the general formula

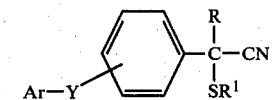

wherein Ar represents an aromatic group, R represents a hydrogen atom or an alkyl group, $R^1$ represents an alkyl group or an aromatic group, and Y represents an oxygen atom or a carbonyl group. The above compound can be prepared by reacting an alpha-aryl-substituted-alpha-thio-acetonitrile of the general formula

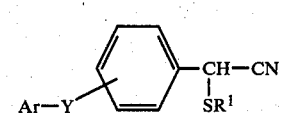

wherein Ar, Y and $R^1$ are as defined above, with an alkylating agent in the presence of a strong base. This compound is useful as an intermediate for producing an alpha-aryl-substituted alkane-carboxylic acid of the general formula

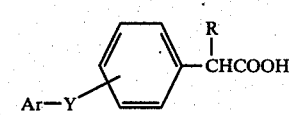

wherein Ar, Y and $R^1$ are as defined above.

3 Claims, No Drawings

ALPHA-THIO-ALPHA-ARYL-SUBSTITUTED ALKANONITRILE AND PROCESS FOR PREPARING ALPHA-ARYL-SUBSTITUTED ALKANONITRILE THEREFROM

This invention relates to alpha-thio-alpha-aryl-substituted alkanonitriles represented by the following general formula

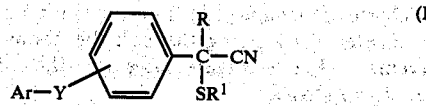

wherein Ar represents an aromatic group, R represents a hydrogen atom or an alkyl group, $R^1$ represents an alkyl group or an aromatic group, and Y represents an oxygen atom or a carbonyl group.

This invention also relates to a process for producing the compounds of formula (I), and a process for preparing other useful compounds therefrom.

The alpha-thio-alpha-aryl-substituted alkanonitriles of general formula (I) are novel compounds not described in the literature. Compounds of general formula (I) in which R is hydrogen can be easily converted to compounds of general formula (I) in which R is an alkyl group by reacting them with alkylating agents in the presence of bases. Reductive desulfurization and hydrolysis of these compounds can easily give alpha-aryl-substituted alkanecarboxylic acids of the following general formula

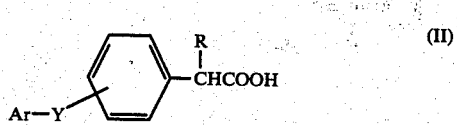

wherein Ar, R and Y are as defined above (see Examples 12 and 13 given hereinbelow). Many of the compounds of general formula (II) have anti-inflammatory, analgesic and anti-pyretic activities. For example, a compound of formula (II) in which R is a methyl, Ar is a phenyl group, Y is oxygen and Ar-Y- is substituted at the meta-position, i.e. alpha-(m-phenoxyphenyl)propionic acid, is so-called "fenoprofen" which is an anti-inflammatory analgesic. A compound of general formula (II) in which R is a methyl group, Ar is a phenyl group and Y is a carbonyl group and Ar-Y- is substituted at the meta-position, i.e. alpha-(m-benzoylphenyl)propionic acid, is "ketoprofen" which is an anti-inflammatory analgesic. A compound of general formula (II) in which R is a methyl group, Ar is a 2-thienyl group, Y is a carbonyl group, and Ar-Y- is substituted at the para-position, i.e. alpha-(p-(2-thienylcarbonyl)phenyl) propionic acid, is known as an anti-inflammatory analgesic, "suprofen".

A number of methods have been suggested in the past for the production of alpha-aryl-substituted alkanecarboxylic acids and their derivatives. Typical processes are illustrated below with reference to the production of fenoprofen and ketoprofen.

The following two processes are known for production of fenoprofen.

Process 1 m-Phenoxyacetophenone is reduced with sodium borohydride to form alpha-(m-phenoxyphenyl)ethyl alcohol which is then reacted with phosphorus tribromide to form alpha-(m-phenoxyphenyl)ethyl bromide. This product is reacted with sodium cyanide under heat in dimethyl sulfoxide. Hydrolysis of the product with sodium hydroxide gives the desired alpha-(m-phenoxyphenyl)propionic acid. (For details, see U.S. Pat. No. 3,600,437).

Process 2 m-Methyldiphenyl ether is brominated with N-bromosuccinimide to obtain m-(bromomethyl)diphenyl ether which is then reacted with sodium cyanide in dimethyl sulfoxide to form m-(cyanomethyl)diphenyl ether. Hydrolysis and esterification of the product afford ethyl alpha-(m-phenoxyphenyl)acetate which is then reacted with diethyl carbonate in the presence of metallic sodium to form diethyl 2-(m-phenoxyphenyl)-malonate. The resulting ester is hydrolyzed to form 2-methyl-2-(m-phenoxyphenyl)malonic acid which is decarboxylated by heating to form alpha-(m-phenoxyphenyl)propionic acid. (For details, see U.S. Pat. No. 3,600,437 and U.S. Pat. No. 3,649,679).

The following processes are available for production of ketoprofen.

Process 1 m-(Bromomethyl)benzophenone is reacted with sodium cyanide to form (m-benzoylphenyl)acetonitrile which is reacted with diethyl carbonate in the presence of sodium ethoxide to form sodium salt of ethyl alpha-cyano(m-benzoylphenyl)acetate. The sodium salt is reacted with methyl iodide to obtain ethyl alpha-cyano-alpha-(m-benzoylphenyl)propionate. The resulting ester is hydrolyzed and then subjected to decarboxylation to form alpha-(m-benzoylphenyl)propionitrile. Alkaline hydrolysis of alpha-(m-benzoylphenyl)propionitrile affords alpha-(m-benzoylphenyl)propionic acid. (For details, see British Patent No. 1,164,585).

Process 2

3-Carboxybenzyne prepared from 2-chlorobenzoic acid in the presence of a strong base is reacted with propionitrile to produce alpha-(m-carboxyphenyl)propionitrile (R. Biehl et al., J. Org. Chem., 31, 602 (1966)). The alpha-(m-carboxyphenyl)propionitrile is converted to alpha-(m-chlorocarbonylphenyl)propionitrile by using thionyl chloride. Friedel-Crafts reaction of alpha-(m-chlorocarbonylphenyl)propionitrile with benzene using aluminum chloride affords alpha-(m-benzoylphenyl)propionitrile. Hydrolysis of the alpha-(m-benzoylphenyl)propionitrile with methanol/sodium hydroxide gives alpha-(m-benzoylphenyl)propionic acid (see British Pat. No. 1,360,560).

In many cases, the starting materials in these prior processes for production of fenoprofen and ketoprofen are difficult to obtain commercially, as is the starting m-phenoxyacetophenone in process 1 for production of fenoprofen. On the other hand, many of arylaldehydes can be easily produced industrially by, for example, the oxidation of the methyl group of the corresponding compounds, the reduction of the corresponding nitrile compounds, ester compounds and acid chlorides, the Vilmeier reaction, the Gattermann method, the Gattermann-Koch method, etc. An industrial method for production of m-phenoxybenzaldehyde which can be a starting material for fenoprofen has already been established (see, for example, U.S. Pat. No. 4,085,147 and U.S. Pat. No. 4,108,904). It has been desired in the art therefore to develop a method for converting an arylaldehyde as a starting material into an alpha-aryl-substituted alkanecarboxylic acid.

The present inventors already invented alpha-aryl-substituted alkanecarboxylic acid derivatives having a thio group at the alpha-position (West Germany DT 2746754), and developed a new method for converting these novel substances into alpha-aryl-substituted alkanecarboxylic acids by alkylation and reductive desulfurization (see West Germany DT No. 2746754). On further investigations, the present inventors arrived at a new process for producing alpha-aryl-substituted alkanecarboxylic acids of general formula (III) above, ent invention has the following advantage. An alpha-aryl-substituted alkanecarboxylic acid of general formula (II) wherein R is an alkyl group can be produced from the aldehyde of general formula (III) by the process which goes through the novel substance of this invention and which comprises five steps. In contrast, the technique of the prior invention of the present inventors requires six steps for production of the alpha-aryl-substituted alkanecarboxylic acid of general formula (II) in which R is an alkyl group from the same aldehyde of formula (III). Thus, the number of steps can be shortened by going through the compound of this invention. The two techniques are schematically compared as follows:

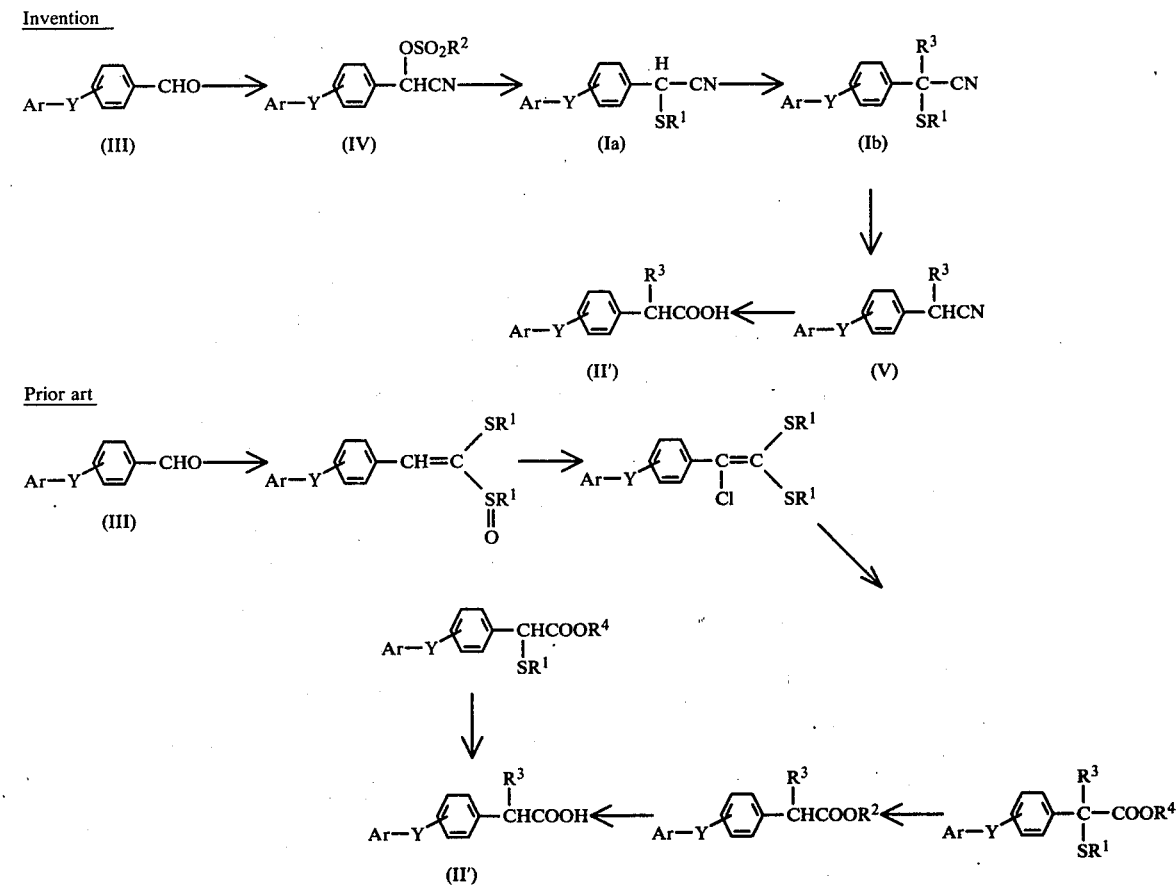

which comprises converting an aromatic aldehyde of the following general formula

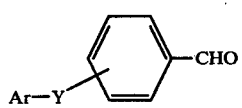

to an alpha-aryl-substituted-alpha-thio-acetonitrile, i.e. a compound of general formula (I) above in which R is a hydrogen atom, converting this compound to a novel compound of formula (I) in which R is an alkyl group, and subsequently subjecting the product to reductive desulfurization and hydrolysis.

When the new technique which goes through the novel substance of this invention is compared with the prior art technique of the present inventors (see West Germany DT No. 2746754), the technique of the pres- Both the technique of this invention and the prior art technique include a step of alkylation. According to the process utilizing the compound of this invention, an industrially advantageous solvent such as methanol and an industrially advantageous base such as sodium methoxide can be used in the alkylation step.

The compound of this invention expressed by general formula (I) can be prepared from the aldehyde (III) in accordance with the following scheme.

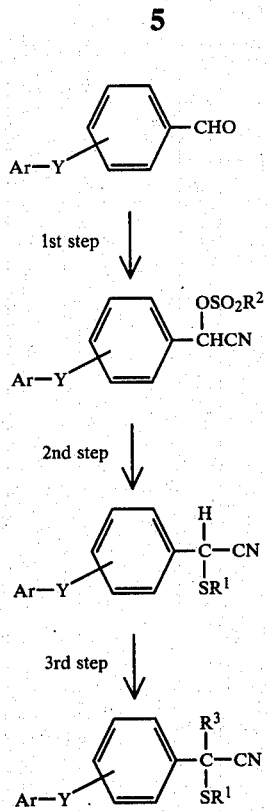

In the above scheme, Ar, Y and $R^1$ are as defined above, $R^2$ represents a lower alkyl group or an aryl group, and $R^3$ represents an alkyl group.

First step (III→IV)

This step comprises the action of an alkali cyanide such as potassium cyanide or sodium cyanide and a sulfonyl chloride ($R^2SO_2Cl$) such as methanesulfonyl chloride or p-toluenesulfonyl chloride to produce an O-sulfonyl-substituted mandelonitrile (IV). The reaction can be achieved by mixing the aldehyde (III), the alkali cyanide and the sulfonyl chloride in nearly equimolar proportions at $-15°$ C. to room temperature using water as a solvent. If desired, the alkali cyanide and the sulfonyl chloride may be used in excessive amounts. It is possible to add an organic solvent which does not participate in the reaction, such as methanol, ethanol, tetrahydrofuran, 1,2-dimethoxyethane, benzene and methylene chloride. A small amount of a surface active agent such as tetrabutylammonium chloride or trimethylbenzylammonium chloride may be added to cause the reaction to proceed smoothly.

Second step (IV→Ia)

This step comprises reacting the O-sulfonyl-substituted mandelonitrile (IV) obtained in the first step with a thiol ($R^1SH$) in the presence of an equimolar amount of a base to give an alpha-thio-alpha-aryl-substituted acetonitrile (Ia). Suitable bases for use in this reaction include alkali metal hydroxides such as sodium hydroxide or potassium hydroxide, alkali metal alkoxides such as sodium methoxide or sodium ethoxide, and alkali metal hydrides such as potassium hydride or sodium hydride. The alkali metal alkoxides and the alkali metal hydroxides are preferred because of their low cost and ease of handling. A wide variety of alkylmercaptans such as methylmercaptan and ethylmercaptan and a wide variety of aromatic mercaptans such as benzenethiol, p-toluenethiol or 2-mercaptobenzothiazole can be used as the thiol. It is sufficient that the thiol is used in an amount substantially equimolar to the O-sulfonyl-substituted mandelonitrile (IV). Alternatively, it is possible to prepare a thiolate anion from the base and the thiol and react the thiolate ion with the O-sulfonyl-substituted mandelonitrile. Examples of the solvent that can be used in this reaction are water, methanol, ethanol, tetrahydrofuran, benzene, dimethylformamide (DMF), and dimethyl sulfoxide (DMSO) which are relatively inert to the reaction. The reaction proceeds smoothly at $-20°$ C. to room temperature. Preferably, the reaction is carried out in an atmosphere of an inert gas such as argon or nitrogen.

Third step (Ia→Ib)

This step comprises reacting the alpha-thio-alpha-aryl-substituted acetonitrile (Ia) obtained in the second step with an alkylating agent in the presence of a base to form a compound of general formula (Ib). Examples of usable bases are metal hydrides such as sodium hydride or potassium hydride, organolithio compounds such as methyllithium or butyllithium, alkali metal amides such as lithium diethylamide or sodium amide, alkali metal alkoxides such as sodium methoxide or sodium ethoxide, and alkali metal hydroxides such as sodium hydroxide or potassium hydroxide. Suitable alkylating agents include alkyl halides such as alkyl iodides or alkyl bromides, and active alkyl esters such as dialkyl sulfates, trialkyl phosphates, alkyl methanesulfonates, or alkyl fluorosulfonates. It is sufficient that the base and the alkylating agent are used in nearly equimolar proportions based on the starting compound (Ia). Protonic solvents such as ethanol or methanol or aprotic solvents such as DMF and DMSO can be used widely in this reaction. The reaction proceeds smoothly at $-20°$ C. to room temperature (about 25° C.). Preferably, it is carried out at 0° C. to room temperature (about 25° C.) because the operation is convenient. To inhibit side-reactions, it is desirable to perform the reaction in an atmosphere of an inert gas such as argon or nitrogen.

The compound of this invention can be easily produced from the aldehyde (III) through the O-sulfonyl-substituted mandelonitrile (IV). Various other methods are available. For example, the compound of this invention can be prepared by reacting a compound of the following general formula

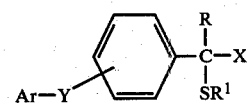

wherein Ar, R, $R^1$ and Y are as defined hereinabove, and X represents halogen or a functional group having the same function as halogen as a leaving group, such as a sulfonyloxy group, with a cyanide anion. It can also be prepared by reacting a compound of the following general formula

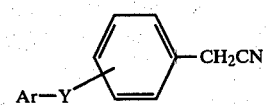

wherein Ar and Y are as defined hereinabove, with a sulfenylating agent such as sulfenyl chloride, sulfenyl cyanide, a disulfide or a thiol ester of sulfonic acid, or a mixture of sulfur and an alkyl halide in the presence of a base. Furthermore, the compound of this invention may be prepared by reacting a compound of the general formula

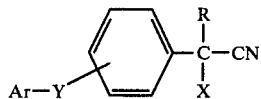

wherein Ar, Y, R and X are as defined above, provided that when R is hydrogen, a sulfonyloxy group is excluded from the definition of X, with a thiol in the presence of a base.

Reductive desulfurization and hydrolysis of the alpha-thio-alpha-aryl-substituted alkanonitrile of general formula (I) which can be thus prepared by various methods can easily afford an alpha-aryl-substituted alkanecarboxylic acid.

The reductive desulfurization can be performed by various methods known in the art, for example, a method involving using an activated nickel metal such as Raney nickel or Urushibara nickel, a method involving using a combination of zinc and an acid or alkali, a method involving use of a combination of tin and an acid, a method involving using a combination of aluminum amalgam and water or a combination of aluminum and a fatty acid such as formic acid or acetic acid, a method involving use of a combination of sodium amalgam and an alcohol, and a method involving use of a thiophile such as a thiolate anion or a phosphite ester. In the method involving using a combination of zinc and an acid or alkali, the reaction will proceed smoothly if zinc is amalgamated or a copper salt is added. The amount of such a reductive desulfurization agent is two reduction equivalents, but it may be used in an excessive amount. The reaction proceeds smoothly at 0° to 100° C. If desired, there can be used a general organic solvent which does not react with the reducing agent, such as acetic acid, methanol, ethanol, tetrahydrofuran, dioxane or benzene. Since the alpha-aryl-substituted alkanonitrile obtained in this step includes a cyano group, any method which tends to induce hydrolysis or reduction of the cyano group will cause some decrease in yield. Accordingly, when the active nickel metal is used, it is desirable to reduce its activity with acetone, etc. before use in the reaction. Furthermore, under the strongly acidic conditions or alkaline conditions as described above, hydrolysis of the cyano group occurs, and the yield of the desired compound is decreased. The by-product at this time is the compound of general formula (II), i.e. alpha-arylsubstituted alkanecarboxylic acid. If the compound of formula (II) is the final desired compound, this method can be applied. From these considerations and from the industrial standpoint, the method involving use of a combination of zinc and a fatty acid, the method involving use of a thiophile, the method involving use of a combination of aluminum or an aluminum-nickel alloy and a fatty acid such as formic acid or acetic acid, the method involving use of a combination of aluminum amalgam and water, the method involving use of a combination of sodium amalgam and an alcohol, and the method involving use of a Raney nickel are the especially preferred methods of reductive desulfurization.

In the compounds of formula (I), the aromatic group Ar is preferably a phenyl or thienyl group; the alkyl group R is preferably an alkyl group having 1 to 4 carbon atoms; and the alkyl group $R^1$ is preferably an alkyl group having 1 to 5 carbon atoms. The aromatic group $R^1$ is a phenyl or benzothiazolyl group optionally substituted with an alkyl group having 1 to 4 carbon atoms.

The following Examples illustrate the present invention more specifically.

EXAMPLE 1

A mixture of 3.96 g of m-phenoxybenzaldehyde and 3.97 g of p-toluenesulfonyl chloride was stirred under ice cooling, and 10 ml of an aqueous solution containing 1.47 g of sodium cyanide was added dropwise over 30 minutes. Then, 10 ml of ethanol was added, and the mixture was stirred for 30 minutes under ice cooling, and then at room temperature for 30 minutes. The mixture was extracted with 30 ml of methylene chloride three times. The extract was washed with 20 ml of water, dried over anhydrous magnesium sulfate, and concentrated under reduced pressure. Recrystallization of the residue from ethanol afforded 3.816 g of O-(p-toluenesulfonyl)-m-phenoxymandelonitrile. The mother liquor was concentrated under reduced pressure, and the residue was purified by column chromatography (silica gel; hexane and benzene) to afford 1.846 g of O-(p-toluenesulfonyl)-m-phenoxymandelonitrile. The total amount of the product was 5.662 g (yield 75%). The product was in the form of colorless crystals.

Melting point: 56–57.5° C. (from ethanol).

IR(KBr): 1600, 1590, 1495, 1490, 1450, 1385, 1260, 1195, 1185, 1005, 1000, 990, 885, 850, 815, 795, 780, 680, 590, 560, 550 cm$^{-1}$.

NMR(CDCl$_3$): δ2.41(3H, s), 5.97(1H, s), 6.8–7.4(11H, m), 8.75(2H, d, J=8Hz).

For $C_{21}H_{17}NO_4S$: Calculated: C, 66.47; H, 4.52; N, 3.69; S, 8.45%. Found: C, 66.44; H, 4.55; N, 3.73; S, 8.58%.

EXAMPLE 2 p-Toluenethiol (5.00 g) was dissolved in 6 ml of methanol, and 1.60 ml of a 2.5 M methanol solution of sodium methoxide was added to the solution at room temperature in a stream of argon. The mixture was stirred under ice cooling. Then, 1.516 g of O-(p-toluenesulfonyl)-m-phenoxymandelonitrile was added, and the mixture was stirred for 30 minutes under ice cooling and then for 10 minutes at room temperature. Water (20 ml) was added, and the mixture was extracted with 30 ml of methylene chloride three times. The extract was washed with 20 ml of water, dried over anhydrous magnesium sulfate, and concentrated under reduced pressure. The residue was purified by column chromatography (silica gel; benzene) to afford 1.334 g (yield 100%) of alpha-(p-tolylthio)(m-phenoxyphenyl)acetonitrile as a colorless oil.

IR(neat): 2250, 1595, 1500, 1450, 1280, 1250, 1215, 820, 800, 755, 700 cm$^{-1}$.

NMR(CDCl$_3$): δ2.30(3H, s), 4.78(1H, s), 6.8–7.4(13H, m).

MS(70 eV): m/e331(48, M+), 209(21), 208(68), 181(100), 123(39), 91(14), 77(24).

EXAMPLE 3

1.245 g of alpha-(p-tolylthio)(m-phenoxyphenyl)-acetonitrile was dissolved in 5 ml of anhydrous methanol, and a 2.2 M methanol solution of sodium methoxide was added at room temperature in an atmosphere of argon. The mixture was stirred, and 0.35 ml of methyl iodide was added dropwise. The mixture was further stirred for 30 minutes at room temperature. Then, an aqueous solution of ammonium chloride (3 g/20 ml) was added, and the mixture was extracted with 20 ml of ether three times. The extract was washed with 30 ml of water three times, dried over anhydrous magnesium sulfate, and concentrated under reduced pressure. The oily residue was purified by column chromatography (silica gel; hexane and methylene chloride) to afford 1.125 g (yield 86%) of alpha-(p-tolylthio)-alpha-(m-phenoxyphenyl)propionitrile as a pale yellow oil.

IR(neat): 1584, 1490, 1256, 1218, 811, 692 cm$^{-1}$.

NMR(CDCl$_3$): 67 1.90(3H, s), 2.28(3H, s), 6.8–7.4(13H, m).

MS(70 eV): m/e345(6, M+), 223(27), 222(75), 221(50), 195(38), 124(100), 123(27), 91(39), 77(51).

EXAMPLE 4

3.79 g of O-(p-toluenesulfonyl)-m-phenoxymandelonitrile was dissolved in 10 ml of anhydrous DMF, and the solution was stirred in an argon atmosphere with ice cooling. Then, 4.35 ml of a 2.3 M methanol solution of sodium methamethiolate was added dropwise over 10 minutes. Under ice cooling, the mixture was stirred for 30 minutes, and 30 ml of water was added. The mixture was extracted with 30 ml of ether three times. The extract was washed with 20 ml of water, dried over anhydrous magnesium sulfate, and concentrated under reduced pressure. The residue was separated and purified by column chromatography (silica gel; hexane and benzene) to afford 1.007 g (yield 39%) of alpha-(methylthio)(m-phenoxyphenyl)acetonitrile as a colorless oil.

IR(neat): 2230, 1590, 1490, 1445, 1270, 1250, 1210, 790, 755, 695 cm$^{-1}$.

NMR(CDCl$_3$): 67 2.18(3H, s), 4.64(1H, s), 6.8–7.4(9H, m).

MS(70 eV): m/e255(62.M+), 209(19), 208(45), 181(100), 149(19), 77(26).

EXAMPLE 5

956 ml of alpha-(methylthio)(m-phenoxyphenyl)-acetonitrile was dissolved in 5 ml of anhydrous methanol, and 1.7 ml of a 2.5 M methanol solution of sodium methoxide was added at room temperature in an atmosphere of argon. The mixture was stirred, and 0.34 ml of methyl iodide was added dropwise. The mixture was further stirred for 1 hour at room temperature. An aqueous solution of ammonium chloride (3 g/20 ml) was added, and the mixture was extracted with 20 ml of ether three times. The extract was washed with 25 ml of water three times, dried over anhydrous magnesium sulfate, and concentrated under reduced pressure. The residue was purified by column chromatography (silica gel; hexane and methylene chloride) to afford 817 mg (yield 82%) of alpha-(methylthio)-alpha-(m-phenoxyphenyl)-propionitrile as a colorless oil.

IR(neat): 2225, 1587, 1494, 1440, 1258, 1219, 696 cm$^{-1}$.

NMR(CDCl$_3$): δ1.90(3H, s), 2.06(3H, s), 6.8–7.4(9H, m).

MS(70 eV): m/e269(40, M+), 222(100), 195(67), 77(38).

EXAMPLE 6 m-Benzoylbenzaldehyde (4.20 g) and 3.80 g of p-toluenesulfonyl chloride were dissolved in 13 ml of 1,2-dimethoxyethane (DME), and the solution was stirred at −15° to −10° C. An aqueous solution of sodium cyanide (1.08 g/15 ml) was added dropwise to the solution over 10 minutes. The mixture was stirred at −15° to −10° C. for 2 hours and then at room temperature for 40 minutes. Water (60 ml) was added, and the mixture was extracted with 60 ml of methylene chloride three times. The extract was washed with 70 ml of water, dried over anhydrous magnesium sulfate, and concentrated under reduced pressure. The residue was separated by column chromatography (silica gel; benzene and methylene chloride) to afford 5.21 g (yield 67%) of O-(p-toluenesulfonyl)-m-benzoylmandelonitrile as colorless crystals.

Melting point: 66.5° to 68° C. (from ethanol).

IR(KBr): 1665, 1390, 1195, 1175, 970, 830, 815, 725, 675, 585, 555 cm$^{-1}$.

NMR(CDCl$_3$): δ2.40(3H, s), 6.13(1H, s), 7.2–7.9(13H, m).

For C$_{22}$H$_{17}$NO$_4$S: Calculated: C, 67.50; H, 4.38; N, 3.58; S, 8.19%.

Found: C, 66.67; H, 4.36; N, 3.58; S, 7.91%.

EXAMPLE 7 p-Toluenethiol (372 mg) was dissolved in 2 ml of anhydrous methanol, and 1.20 ml of a 2.5 M methanol solution of sodium methoxide was added at room temperature in an atmosphere or argon. The mixture was cooled to −15° C., and stirred. Then, 4 ml of an anhhdrous DMF solution containing 1.170 g of O-(p-toluenesulfonyl)-m-benzoylmandelonitrile was added over 10 minutes. With continued stirring, the mixture was gradually warmed, and in 30 minutes, the temperature rose to 0° C. At this time, 30 ml of water was added to the reaction mixture, and the mixture was extracted with 20 ml of methylene chloride three times. The extract was washed with 20 ml of water, dried over anhydrous magnesium sulfate, and concentrated under reduced pressure. The residue was purified by column chromatography (silica gel; benzene) to afford 837 mg (yield 82%) of alpha-(p-tolylthio)(m-benzoylphenyl)acetonitrile as colorless crystals.

Melting point: 79°–79.5° C. (from ethanol).

IR(KBr): 2230, 1650, 1600, 1495, 1450, 1325, 1315, 1300, 810, 790, 715 cm$^{-1}$.

NMR(CDCl$_3$): δ2.35(3H, s), 4.98(1H, s), 6.9–7.9(13H, m).

MS(70 eV): m/e343(21, M+), 221(14), 220(37), 165(28), 123(100), 105(44), 91(15), 77(45).

For C$_{22}$H$_{17}$NOS: Calculated: C, 76.93; H, 4.99; N, 4.08; S, 9.34%. Found: C, 76.91; H, 5.01; N, 3.97; S, 9.37%.

EXAMPLE 8

Anhydrous methanol (2 ml) was added to 439 mg of alpha-(p-tolylthio)(m-benzoylphenyl)acetonitrile, and the mixture was stirred under ice cooling. Then, 0.55 ml of a 2.5 M methanol solution of sodium methoxide was added, and 0.12 ml of methyl iodide was added dropwise. The mixture was further stirred for 30 minutes at room temperature. An aqueous solution of ammonium chloride (0.5 g/20 ml) was added, and the mixture was extracted with 15 ml of methylene chloride three times. The extract was washed with 10 ml of water, dried over anhydrous magnesium sulfate, and concentrated under reduced pressure to afford an oily residue. The residue was purified by column chromatography (silica gel; benzene) to afford 422 mg (yield 92%) of alpha-(p-tolylthio)-alpha-(m-benzoylphenyl)propionitrile as a colorless oil.

IR(neat): 2230, 1665, 1600, 1495, 1450, 1325, 1285, 1225, 815, 715 cm$^{-1}$.

NMR(CDCl$_3$): δ 1.96(3H, s), 2.26(3H, s), 6.9–7.9(13H, m).

MS(70 eV): m/e 357(6, M$^{30}$), 234(74), 124(100), 105(72), 91(23), 77(58).

EXAMPLE 9

979 mg of O-(p-toluenesulfonyl)-m-benzoylmandelonitrile was dissolved in 2 ml of DMF, and the mixture was stirred in an argon atmosphere under ice cooling. Then, 1.08 ml of a 2.3 M methanol solution of sodium methanethiolate was added dropwise to the solution over 5 minutes, and the mixture was further stirred under ice cooling. An aqueous solution of ammonium chloride (0.2 g/30 ml) was added, and the mixture was extracted with methylene chloride. The extract was washed with 10 ml of water, dried over anhydrous magnesium sulfate, and concentrated under reduced pressure. The oily residue was separated by column chromatography (silica gel; methylene chloride) to afford 533 mg (yield 80%) of alpha-(methylthio)(m-benzoylphenyl)acetonitrile as a pale orange oil.

IR(neat): 2230, 1665, 1605, 1455, 1325, 1290, 715, 700 cm$^{-1}$.

NMR(CDCl$_3$): δ2.23(3H, s), 4.82(1H, s), 7.3–8.0(9H, m).

MS(70 eV): m/e 267(12, M+), 222(15), 221(91), 220(81), 193(24), 165(74), 115(19), 105(100), 77(93).

EXAMPLE 10

433 mg of alpha-(methylthio)(m-benzoylphenyl)acetonitrile was dissolved in 2 ml of anhydrous methanol. The solution was stirred in an atmosphere of argon under ice cooling. Then, 0.65 ml of a 2.5 M methanol solution of sodium methoxide was added, and then 0.15 ml of methyl iodide was added dropwise. Under ice cooling, the mixture was stirred for 1 hour, and an aqueous solution of ammonium chloride (0.5 g/30 ml) was added. The mixture was extracted with 20 ml of methylene chloride three times. The extract was washed with 10 ml of water, dried over anhydrous magnesium sulfate, and concentrated under reduced pressure. The residue was purified by column chromatography (silica gel; methylene chloride) to afford 334 mg (yield 73%) of alpha-(methylthio)-alpha-(m-benzoylphenyl)-propionitrile as a pale yellow oil.

IR(neat): 2225, 1665, 1600, 1450, 1325, 1285, 720, 705, 695 cm$^{-1}$.

NMR(CDCl$_3$): 1.97(3H, s), 2.10(3H, s), 7.3–8.1(9H, m).

MS(70 eV): 281(8, M+), 235(32), 234(100), 207(12), 179(16), 149(10), 105(47), 77(48).

EXAMPLE 11

795 mg of O-(p-toluenesulfonyl)-p-(2-thienylcarbonyl)mandelonitrile was dissolved in 3 ml of anhydrous DMF, and the solution was stirred at −15° C. in an argon atmosphere. A solution prepared by adding 0.80 ml of a 2.5 M methanol solution of sodium methoxide at room temperature to 2 ml of an anhydrous methanol solution containing 250 mg of p-toluenethiol was added dropwise over the course of 10 minutes. After the addition, the mixture was further stirred, and its temperature was gradually raised to bring it to −5° C. in 20 minutes. At this time, an aqueous solution of ammonium chloride (1 g/30 ml) was added to the reaction mixture, and the mixture was extracted with 20 ml of methylene chloride three times. The extract was washed with 20 ml of water, dried over anhydrous magnesium sulfate, and concentrated under reduced pressure. The residue was recrystallized from ethanol to afford 387 mg of alpha-[p-tolylthio][p-(2-thienylcarbonyl)phenyl]acetonitrile as colorless crystals. The mother liquor was concentrated under reduced pressure, and the residue was separated by column chromatography (silica gel; methylene chloride) to afford 95 mg of alpha(p-tolylthio)[p-(2-thienylcarbonyl)phenyl]acetonitrile.

The total amount of the products yielded was 482 mg, and the yield was 69%.

Melting point: 124°–126° C. (from ethanol).

IR(KBr): 2230, 1635, 1610, 1420, 1355, 1295, 1240, 1050, 885, 810, 735 cm$^{-1}$.

NMR(CDCl$_3$): δ2.33(3H, s), 4.95(1H, s), 7.0–7.9(11H, m).

For C$_{20}$H$_{15}$NOS$_2$: Calculated: C, 68.74; H, 4.33; N, 4.01; S, 18.35%.

Found: C, 68.95; H, 4.27; N, 4.02. S, 18.41%.

EXAMPLE 12

Anhydrous methanol (3 ml) was added to 351 mg of alpha-(p-tolylthio)[p-(2-thienylcabonyl)phenyl]acetonitrile, and the mixture was stirred in an argon atmosphere under ice cooling. Then, 0.45 ml of a 2.5 M methanol solution of sodium methoxide was added, and 0.10 ml of methyl iodide was added dropwise. The temperature was brought to room temperature and the mixture was stirred for 15 minutes. An aqueous solution of ammonium chloride (0.2 g/30 ml) was added, and the mixture was extracted with 20 ml of methylene chloride three times. The extract was washed with 20 ml of water, dried over anhydrous magnesium sulfate; and concentrated under reduced pressure. The residue was purified by column chromatography (silica gel; methylene chloride) to afford 314 mg (yield 86%) of alpha-(p-tolylthio)-alpha-[p-(2-thienylcabonyl)phenyl]-propionitrile as colorless crystals.

Melting point: 113°–114° C. (from ethanol).

IR(KBr): 2230, 1625, 1420, 1300, 850, 815, 735 cm$^{-1}$.

NMR(CDCl$_3$): δ2.01(3H, s), 2.30(3H, s), 7.0–7.9(11H, m).

For C$_{21}$H$_{17}$NOS$_2$: Calculated: C, 69.39; H, 4.72; N, 3.85; S, 17.64%. Found: C, 69.31; H, 4.75; N, 3.84; S, 17.79%.

EXAMPLE 13

417 mg of alpha-(p-tolylthio)-alpha-(m-phenoxyphenyl)propionitrile was dissolved in 4 ml of acetic acid. Zinc powder (370 mg) and 25 mg of anhydrous copper sulfate were added. The mixture was heated under reflux for 1 hour with stirring. After the cooling, 20 ml of water and 20 ml of ether were added. The insoluble matter was separated by filtration. Sodium carbonate (5 g) was added to the filtrate to neutralize the acetic acid, followed by extraction with ether (15 ml×4 times). The extract was washed with 30 ml of water three times, dried over anhydrous magnesium sulfate, and concentrated under reduced pressure. The oily residue was purified by column chromatography (silica gel; hexane and methylene chloride) to afford 247 mg (yield 92%) of alpha-(m-phenoxyphenyl)propionitrile as an oil. A sample for elemental analysis was prepared by subjecting the oil to bulb-to-bulb distillation [149°–154° C. (bath temperature)/1 torr].

IR(neat): 2225, 1588, 1491, 1249, 1210, 1160, 932, 693 cm$^{-1}$.

NMR(CDCl$_3$): δ1.56(3H, d, J=7Hz), 3.78(1H, q, J=7Hz), 6.9–7.4(9H, m).

MS(70 eV): m/e224(17), 223(100, M+), 181(26), 77(26).

For C$_{15}$H$_{13}$NO: Calculated: C, 80.68; H, 5.88; N, 6.27%. Found: C, 80.52; H, 5.89; N, 6.12%.

EXAMPLE 14

Ethanol (5 ml) and 1 ml of water were added to 191 mg of alpha-(m-phenoxyphenyl)propionitrile, and 490 mg of potassium hydroxide was added. The mixture was heated under reflux for 5 hours. The reaction mixture was cooled, and 10 ml of water was added. The mixture was washed with 10 ml of ether three times. Conc. hydrochloric acid was added to the aqueous layer to adjust its pH to below 1, and then it was extracted with 10 ml of ether three times. The extract was washed with 20 ml of water two times, dried over anhydrous magnesium sulfate, and concentrated under reduced pressure. The residue was purified by column chromatography (silica gel; methylene chloride and ether) to afford 187 mg (yield 90%) of alpha-(m-phenoxyphenyl)-propionic acid as a colorless oil. The IR spectrum of this product coincided completely with that of an authentic sample.

EXAMPLE 15

Butylmercaptan (105 mg) was dissolved in 1 ml of methanol, and 0.4 ml of a 2.7 M methanol solution of sodium methoxide was added at room temperature. The solution was added dropwise to 2 ml of a 1,2-dimethoxyethane solution of 391 mg of O-(p-toluenesulfonyl)-m-benzoylmandelonitrile in an argon atmosphere under ice cooling. The mixture was stirred for 1 hour under ice cooling, and 20 ml of water was added. The mixture was extracted with 20 ml of methylene chloride three times. The extract was washed with 10 ml of water, dried over anhydrous magnesium sulfate, and concentrated under reduced pressure. The residue was separated by column chromatography (silica gel; benzene) to afford 95 mg (yield 31%) of alpha-(butylthio)(m-benzoylphenyl)acetonitrile as a colorless oil.

IR(neat): 2230, 1670, 1600, 1450, 1325, 1290, 715, 650 cm$^{-1}$.

NMR(CDCl$_3$): δ0.8–1.0(3H, m), 1.2–2.8(4H, m), 2.5–2.9(2H, m), 4.83(1H, s), 7.3–7.9(9H, m).

EXAMPLE 16

90 mg of alpha-(butylthio)(m-benzoylphenyl)acetonitrile was dissolved in 1 ml of anhydrous methanol, and 0.15 ml of a 2.7 M methanol solution of sodium methoxide was added in an atmosphere of argon under ice cooling, followed by addition of 0.05 ml of methyl iodide. The temperature of the mixture was brought to room temperature, and the mixture was stirred for 30 minutes. Water (20 ml) was added, and the mixture was extracted with 20 ml of ether three times. The extract was washed with 10 ml of water, dried over anhydrous magnesium sulfate, and concentrated under reduced pressure. The residue was purified by column chromatography (silica gel; benzene) to afford 82 mg (yield 87%) of alpha-(butylthio)-alpha-(m-benzoylphenyl)propionitrile as a colorless oil.

IR(neat): 2225, 1670, 1605, 1455, 1325, 1290, 720 cm$^{-1}$.

NMR(CDCl$_3$): δ0.7–0.9(3H, m), 1.1–1.7(4H, m), 1.94(3H, s), 2.2–2.8(2H, m), 7.3–9.1(9H, m).

EXAMPLE 17

451 mg of alpha-(methylthio)-alpha-(m-phenoxyphenyl)propionitrile was dissolved in 1 ml of anhydrous methanol, and 1.1 ml of a 2.3 M methanol solution of sodium methanethiolate was added. The mixture was stirred at room temperature for 2 hours. An aqueous solution of ammonium chloride (2 g/10 ml) was added, and the mixture was extracted with 10 ml of ether three times. The extract was washed with 15 ml of water three times, dried over anhydrous magnesium sulfate, and concentrated under reduced pressure. The residue was purified by column chromatography (silica gel; hexane and methylene chloride) to afford 316 mg (yield 83%) of alpha-(m-phenoxyphenyl)-propionitrile as a colorless oil.

EXAMPLE 18

314 mg of alpha-(p-tolylthio)-alpha-(m-benzoylphenyl)propionitrile was dissolved in 1 ml of methanol, and 1.0 ml of a 2.3 M methanol solution of sodium methanethiolate was added dropwise. The mixture was stirred at room temperature for 1 hour. An aqueous solution of ammonium chloride (1 g/5 ml) was added, and the mixture was extracted with 10 ml of ether three times. The extract was washed with 15 ml of water three times, dried over anhydrous magnesium sulfate, and concentrated under reduced pressure. The residue was purified by column chromatography (silica gel; benzene and methylene chloride) to afford 133 mg (yield 64%) of alpha-(m-benzoylphenyl)-propionitrile as colorless crystals.

Melting point: 54°–55° C. (from ethanol).

IR(KBr): 2225, 1660, 1605, 1600, 1450, 1325, 1295, 1265, 725, 710, 700, 690 cm$^{-1}$.

NMR(CDCl$_3$): δ1.62(3H, d, J=7 Hz), 3.93(1H, q, J=7 Hz), 7.3–7.8(9H, m).

MS(70 eV): m/e235(25, M+), 158(30), 105(100), 77(42).

For C$_{16}$H$_{13}$NO: Calculated: C, 81.67; H, 5.58; N, 5.95%. Found: C, 81.78; H, 5.56; N, 5.87%.

EXAMPLE 19

241 mg of alpha-(methylthio)-alpha-(m-benzoylphenyl)propionitrile was dissolved in 1 ml of methanol, and 0.60 ml of a 2.3 M methanol solution of sodium methanethiolate was added dropwise. The mixture was stirred at room temperature for 1.5 hours. An aqueous solution of ammonium chloride (2 g/10 ml) was added, and the mixture was extracted with 10 ml of ether three times. The extract was washed with 20 ml of water three times, dried over anhydrous magnesium sulfate, and concentrated under reduced pressure. The residue was purified by column chromatography (silica gel; methylene chloride) to afford 167 mg (yield 79%) of alpha-(m-benzoylphenyl)propionitrile.

EXAMPLE 20

Methanol (6 ml) and 3 ml of DME were added to 1.18 g of O-(p-toluenesulfonyl)-m-benzoylmandelonitrile, and the mixture was stirred in an argon atmosphere under ice cooling. Sodium salt of 2-mercaptobenzothiazole (570 mg) was added, and the mixture was stirred for 1.5 hours under ice cooling. Water (50 ml) was added, and the mixture was extracted with 30 ml of methylene chloride three times. The extract was washed with 40 ml of water, dried over anhydrous magnesium sulfate, and concentrated under reduced pressure. The residue was separated by column chromatography (silica gel; methylene chloride) to afford 972 mg (yield 83%) of alpha-(2-benzothiazolylthio)-(m-benzoylphenyl)acetonitrile as a pale yellow oil.

IR(neat): 2240, 1665, 1600, 1585, 1465, 1450, 1430, 1325, 1315, 1290, 1180, 1075, 1020, 1000, 815, 790, 760, 715, 700, 645 cm$^{-1}$.

NMR(CDCl$_3$): δ6.15(1H, s), 7.1–8.2(13H, m).

EXAMPLE 21

Methanol (3 ml) and 2 ml of DME were added to 802 mg of alpha-(2-benzothiazolylthio)(m-benzoylphenyl)acetonitrile, and the mixture was stirred in an argon atmosphere under ice cooling. Then, 0.78 ml of a 2.7 M methanol solution of sodium methoxide was added, and then 0.19 ml of methyl iodide was added dropwise. The reaction mixture was stirred at room temperature for 1 hour, and after adding an aqueous solution of ammonium chloride (1 g/20 ml), extracted with 40 ml of methylene chloride three times. The extract was washed with 50 ml of water, dried over anhydrous magnesium sulfate, and concentrated under reduced pressure. The residue was separated by column chromatography (silica gel; benzene and methylene chloride) to afford 580 mg (yield 70%) of alpha-(2-benzothiazolylthio)-alpha-(m-benzoylphenyl)propionitrile as an oil.

IR(neat): 2230, 1675, 1665, 1605, 1590, 1465, 1455, 1440, 1325, 1290, 1230, 1080, 995, 765, 720, 705, 695 cm$^{-1}$.

NMR(CDCl$_3$): δ2.24(3H, s), 7.2–8.3(13H, m).

EXAMPLE 22

1.18 g of O-(p-toluenesulfonyl)-m-benzoylmandelonitrile was dissolved in a mixture of 4 ml of methanol and 3 ml of DME, and the solution was stirred in an argon atmosphere under ice cooling. Sodium salt of 2-mercaptobenzothiazole (570 mg) was addded, and the mixture was stirred for 1 hour under ice cooling. Then, 1.15 ml of a 2.7 M methanol solution of sodium methoxide was added, and 0.22 ml of methyl iodide was further added dropwise. The temperature was brought to room temperature, and the solution was stirred for 1 hour. An aqueous solution of ammonium chloride (1 g/20 ml) was added, and the mixture was extracted with 40 ml of methylene chloride three times. The extract was washed with 40 ml of water, dried over anhydrous magnesium sulfate, and concentrated under reduced pressure. The residue was separated by column chromatography (silica gel; benzene and methylene chloride) to afford 892 mg (yield 74%) of alpha-(2-benzothiazolylthio)-alpha-(m-benzoylphenyl)propionitrile.

EXAMPLE 23

1.191 g of O-(p-toluenesulfonyl)-p-(2-thienylcarbonyl)mandelonitrile was dissolved in 5 ml of DME, and the solution was stirred in an argon atmosphere under ice cooling. Sodium salt of 2-mercaptobenzothiazole (567 mg) was added, and the mixture was stirred under ice cooling for 45 minutes, and then at room temperature for 30 minutes. Water (30 ml) was added, and the mixture was extracted with 30 ml of methylene chloride three times. The extract was washed with 20 ml of water, dried over anhydrous magnesium sulfate, and concentrated under reduced pressure. The residue was separated by column chromatography (silica gel; methylene chloride) to afford 788 mg (yield 67%) of alpha-(2-benzothiazolylthio)[p-(2-thienylcarbonyl)phenyl] acetonitrile as a viscous oil.

IR(neat): 2240, 1645, 1430, 1420, 1295, 995, 760, 725 cm$^{-1}$.

NMR(CDCl$_3$): δ6.22(1H, s), 7.0–8.1(11H, m).

EXAMPLE 24

Methanol (5 ml) and 1 ml of DME were added to 788 mg of alpha-(2-benzothiazolylthio)[p-(2-thienylcarbonyl)phenyl]acetonitrile, and the mixture was stirred in an argon atmosphere under ice cooling. Methyl iodide (0.20 ml) and 0.81 ml of a 2.7 M methanol solution of sodium methoxide were added. The mixture was stirred under ice cooling for 1 hour, and then at room temperature for 3.5 hours. Water (20 ml) and 30 ml of methylene chloride were added, and the insoluble matter was removed by filtration. The filtrate was shaken, and the organic layer was separated. The aqueous layer was extracted with 20 ml of methylene chloride twice. The organic layers were combined, washed with 20 ml of water, dried over anhydrous magnesium sulfate, and concentrated under reduced pressure. The residue was separated by column chromatography (silica gel; methylene chloride) to afford 73 mg of alpha-(2-benzothiazolylthio)alpha-[p-(2-thienylcarbonyl)phenyl]propionitrile as colorless crystals.

Melting point: 104° to 107° C. (from ethanol).

IR(KBr): 1630, 1415, 1295, 980, 760, 725 cm$^{-1}$.

NMR(CDCl$_3$): 2.23(3H, s), 7.0–8.1(7H, m), 7.84(4H, s).

EXAMPLE 25

1.517 g of O-[p-toluenesulfonyl)-m-phenoxymandelonitrile was dissolved in 5 ml of DME, and the solution was stirred in an argon atmosphere under ice cooling. Sodium salt of 2-mercaptobenzothiazole (760 mg) was added, and the mixture was stirred under ice cooling for 30 minutes, and then at room temperature for 1.5 hours. Water (20 ml) was added to the reaction mixture, and it was extracted with 20 ml of methylene chloride three times. The extract was washed with 10 ml of water, dried over anhydrous magnesium sulfate, and concentrated under reduced pressure. The residue was purified by column chromatography (silica gel; benzene and methylene chloride) to afford 1.233 g (yield 85%) of alpha-(2-benzothiazolylthio)(m-phenoxyphenyl)acetonitrile as a colorless oil.

IR(neat): 2230, 1585, 1490, 1460, 1455, 1430, 1270, 1250, 1210, 1000, 760, 695 cm$^{-1}$.

NMR(CDCl$_3$): δ6.03(1H, s), 6.9–7.6(11H, m), 7.7–8.0(2H, m).

EXAMPLE 26

Methanol (5 ml) was added to 945 mg of alpha-(2-benzothiazolylthio)(m-phenoxyphenyl)acetonitrile, and the mixture was stirred under ice cooling in an argon atmosphere. Then, 1.0 ml of a 2.7 M methanol solution of sodium methoxide was added, and the mixture was stirred under ice cooling for 10 minutes. Methyl iodide (0.25 ml) was then added. The mixture was stirred under ice cooling for 30 minutes, and then at room temperature for 2.5 hours. Then, 30 ml of water was added, and the reaction mixture was extracted with 20 ml of methylene chloride three times. The extract was washed with 10 ml of water, dried over anhydrous magnesium sulfate, and concentrated under reduced pressure. The residue was purified by column chromatography (silica gel; benzene and methylene chloride) to afford 752 mg (yield 77%) of alpha-(2-benzothiazolylthio)-alpha-(m-phenoxyphenyl)propionitrile as an oil.

IR(neat): 2230, 1590, 1495, 1260, 1220, 990, 790, 765, 695 cm$^{-1}$.

NMR(CDCl$_3$): $\delta$2.19(3H, s), 6.8-7.6(11H, m), 7.7-7.9(1H, m), 7.9-8.1(1H, m).

EXAMPLE 27

Anhydrous methanol (4 ml) was added to 524 mg of alpha-(2-benzothiazolythio)-alpha-(m-benzoylphenyl)-propionitrile, and the mixture was stirred at room temperature. 1.14 ml of a 2.3 M methanol solution of sodium methamethiolate was added dropwise, and the mixture was stirred at room temperature for 45 minutes. An aqueous solution of ammonium chloride (1 g/20 ml) was added, and the mixture was extracted with 50 ml of ether three times. The extract was washed with 40 ml of water, dried over anhydrous magnesium sulfate, and concentrated under reduced pressure. The residue was separated and purified by column chromatography (silica gel; methylene chloride) to afford 264 mg (yield 86%) of alpha-(m-benzoylphenyl)-propionitrile as colorless crystals.

Melting point: 54°-55° C. (from ethanol)

IR(KBr): 2225, 1660, 1605, 1600, 1450, 1325, 1295, 1265, 725, 710, 700, 690 cm$^{-1}$.

NMR(CDCl$_3$): $\delta$1.62(3H, d, J=7 Hz), 3.93(1H, q, J=7 Hz), 7.3-7.8(9H, m).

MS(70 eV): m/e235(25, M$^+$), 158(30), 105(100), 77(42).

For C$_{16}$H$_{13}$NO: Calculated: C, 81.67; H, 5.58; N, 5.95%. Found: C, 81.78; H, 5.56; N, 5.87%.

EXAMPLE 28

Methanol (1 ml) and 1 ml of water were added to 200 mg of alpha-(m-benzoylphenyl)propionitrile, and 50 mg of sodium hydroxide was added. The mixture was heated under reflux for 24 hours. The reaction mixture was cooled, and after adding 10 ml of water, extracted with 5 ml of ether three times. The extract was washed with 5 ml of water three times. The aqueous layers were combined, and after adding conc. hydrochloric acid to adjust the pH to below 1, were extracted with 5 ml of ether three times. The extract was washed with 5 ml of water, dried over anhydrous magnesium sulfate, and concentrated under reduced pressure. The oily residue was purified by column chromatography (silica gel; methylene chloride and ethyl acetate) to afford 181 mg (yield 84%) of alpha-(m-benzoylphenyl)propionic acid as colorless crystals. The IR spectrum and NMR spectrum of the product coincided completely with those of an authentic sample.

What we claim is:

1. An alpha-thio-alpha-aryl-substituted alkanonitrile of the formula

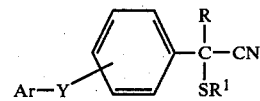

wherein Ar represents phenyl or thienyl, R represents hydrogen or alkyl, R$^1$ represents alkyl, phenyl, phenyl substituted by alkyl having 1 to 4 carbon atoms, or 2-benzothiazolyl, and Y represents oxygen or carbonyl.

2. The compound of claim 1 wherein the alkyl group R has 1 to 4 carbon atoms, and the alkyl group R$^1$ has 1 to 5 carbon atoms.

3. The compound of claim 1 wherein R represents hydrogen or methyl.

* * * * *